United States Patent
Mikus et al.

[11] Patent Number: 6,033,413
[45] Date of Patent: Mar. 7, 2000

[54] STENT DELIVERY SYSTEM

[75] Inventors: Paul W. Mikus; Jay Eum, both of Irvine, Calif.

[73] Assignee: Endocare, Inc., Irvine, Calif.

[21] Appl. No.: 09/063,118

[22] Filed: Apr. 20, 1998

[51] Int. Cl.⁷ ..................................................... A61F 11/00
[52] U.S. Cl. ........................ 606/108; 606/192; 604/102
[58] Field of Search ........................................ 606/108, 191, 606/192, 193; 604/99, 101, 102; 600/587, 135, 136, 139, 462, 463, 466, 469, 470

[56] References Cited

U.S. PATENT DOCUMENTS

| | | | |
|---|---|---|---|
| 4,154,244 | 5/1979 | Becker et al. | 128/349 |
| 4,239,042 | 12/1980 | Asai | 128/214.4 |
| 4,448,195 | 5/1984 | LeVeen et al. | 128/344 |
| 4,456,011 | 6/1984 | Warnecke | 128/325 |
| 4,762,128 | 8/1988 | Rosenbluth | 606/192 |
| 4,820,349 | 4/1989 | Saab | 128/344 |
| 4,906,244 | 3/1990 | Pinchuk et al. | 606/194 |
| 4,938,676 | 7/1990 | Jackowski et al. | 425/140 |
| 4,950,239 | 8/1990 | Gahara et al. | 604/96 |
| 5,002,558 | 3/1991 | Klein et al. | 604/102 |
| 5,344,425 | 9/1994 | Sawyer | 606/198 |
| 5,391,172 | 2/1995 | Williams et al. | 606/108 |
| 5,599,326 | 2/1997 | Carter | 604/282 |
| 5,599,492 | 2/1997 | Engelson | 264/167 |
| 5,601,591 | 2/1997 | Edwards et al. | 606/198 |

*Primary Examiner*—Michael Buiz
*Assistant Examiner*—Lien Ngo
*Attorney, Agent, or Firm*—K. David Crockett, Esq.; Crockett & Crockett

[57] ABSTRACT

A stent delivery system for use in placing a stent within the prostatic urethra and ensuring that the stent does not interfere with the closure of the bladder neck sphincter. The delivery system includes a catheter with an anchor which anchors the catheter within the urethra and ensures placement of the stent at a predetermined distance from the bladder neck sphincter. For use with shape memory stents, the catheter includes a warming fluid system in which the endoscope used in the procedure can act as a fluid supply line and as valve spool to control the flow or warming fluid to the stent.

8 Claims, 13 Drawing Sheets

STENT DELIVERY SYSTEM

FIELD OF THE INVENTION

This invention relates to stent delivery systems to facilitate the treatment for benign prostate hypertrophy or prostate cancer.

BACKGROUND OF THE INVENTION

Prostate enlargement, also known as benign prostate hyperplasia or benign prostate hypertrophy, is a common affliction among older men. The condition involves swelling of the prostate. The prostate surrounds the urethra, or urinary tract, and swelling of the prostate prevents passage of urine from the bladder. Benign prostate hyperplasia is uncomfortable because it makes urination difficult or impossible. The condition is also dangerous because it can lead to infection of the bladder and kidneys, and severe cases may lead to death. Prostate cancer is also a common affliction among older men, and may lead to many of the same symptoms as benign prostate enlargement. Prostate cancer is more dangerous in that it may spread to other organs and is often fatal. Early treatment can reduce the risks of death due to prostate cancer.

Both prostate enlargement and prostate cancer can be treated with heat treatments such as hyperthermia or thermotherapy. As described in our co-pending U.S. application Ser. No. 08/629,650 filed Apr. 9, 1996, a stent serves the dual purpose of acting as a heat source for the thermotherapy procedures, as well as acting to hold the urethra open after therapy to prevent blockage due to swelling and prostate tissue sloughing. A stent may be implanted as an interim solution to hold open the urethra while the patient awaits more aggressive surgery or treatment. A stent may be implanted after hypothermia or cryosurgery to keep the urethra open while enlargement subsides. Finally, a stent may be implanted as a primary treatment.

When the stent is implanted for any of these reasons, it is usually better to leave the bladder neck sphincter and the external sphincter un-blocked by the stent. These sphincters control the flow of urine through the urethra, and if the stent is placed within these sphincters they will not be able to close. This would leave the patient incontinent. To ensure the proper positioning of the stent, the devices below provide several benefits including visualization of the bladder and prostatic urethra during placement, anchoring of the insertion catheter in place during insertion, and distal-first deployment of the stent.

SUMMARY

The stent delivery systems described below permit placement of stents in the urethra. The devices are intended to deploy a shape memory stent into the prostatic urethra under direct vision. The surgeons who use the stent delivery systems can easily place the stent within the prostatic urethra and make sure that the stent does not block the bladder neck sphincter. This is accomplished by anchoring the stent insertion catheter within the bladder, locating the stent under direct vision, and expanding the stent from the distal end first, then expanding the proximal end. Direct vision is accomplished by use of an endoscope in the central lumen of the insertion catheter which has a transparent catheter wall. The insertion catheter has a valved tip which permits the use of the central lumen with an insertion guidewire to assist in pushing the device into the prostatic urethra, but also provides for closure of the central lumen so that water may be injected through the catheter and will preferentially flow out of the catheter through vent ports which direct flow to the stent. The vent ports are blocked or throttled by the endoscope until the endoscope is pulled proximally in the central lumen to open vent ports to a fluid supplied into the central lumen through the working channel of the endoscope. The device may be provided as a disposable item which is generally composed of a catheter with a mesh basket, a toroidal shaped balloon or a malecot attached at its distal end which serves to anchor the device in place, a stent mounted near the distal end of the catheter, a proximal manifold of ports supplying necessary access for endoscopes and fluid injection, and a peel-away protective sheath, all designed for use with standard endoscopes.

DETAILED DESCRIPTION OF THE INVENTION

Figure 1:
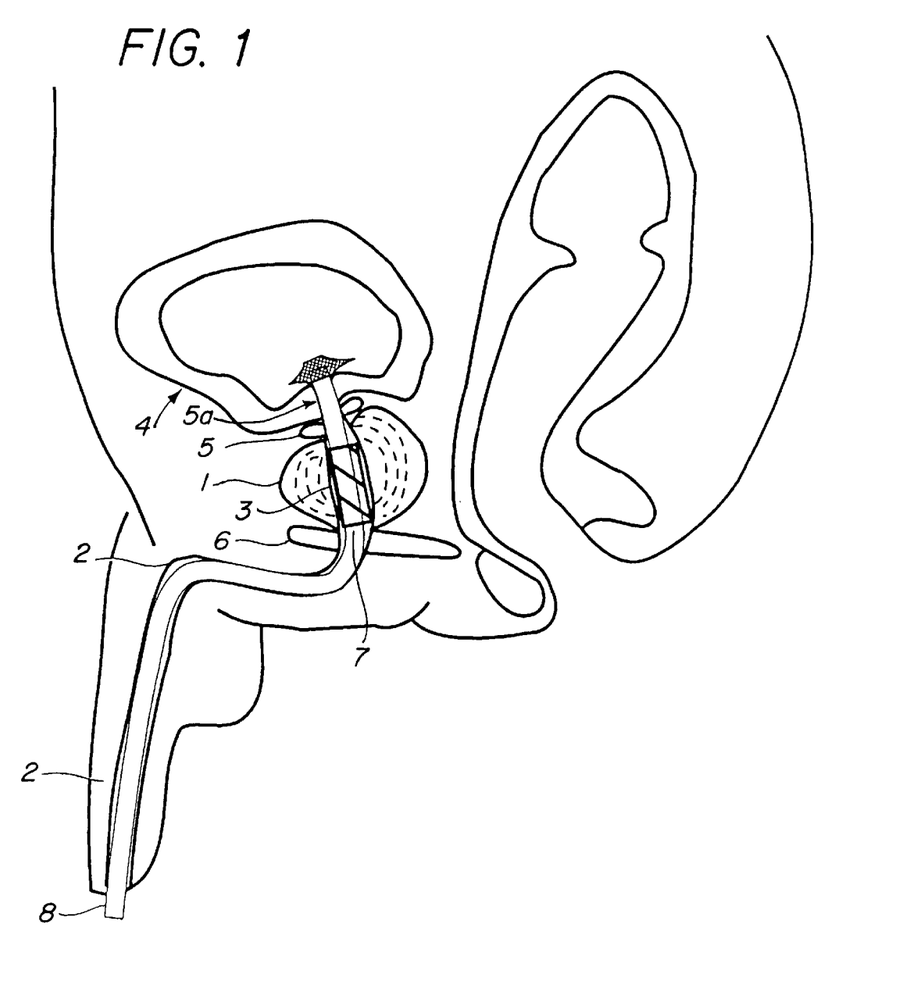
FIG. 1 is a cross-sectional view of the lower abdominal portion of the human body with a stent delivery system in place.

FIG. 1 shows a schematic representation of the stent delivery system designed for use in the treatment of benign prostate hyperplasia or prostate cancer in place within the human body. The details of the local anatomy shown in FIG.

1 include the prostate gland 1, the urethra 2, the prostatic urethra 3, and the bladder 4. The urethra 2 is the channel which conducts urine from the bladder 4 to the penis for discharge from the body. The prostatic urethra 3 is a continuation of the urethra 2, and it joins the prostate gland 1 to the urethra 2. The bladder neck sphincter 5 controls flow of urine from the bladder 4 through the bladder neck 5*a*. The external sphincter 6 controls flow of urine or ejaculate from the bladder 4 or prostate 1. The inside diameter of urethra 2 is typically about 2 cm, and the prostatic urethra 3 varies in length from about 15 to 75 mm.

The stent 7 is delivered to the prostatic urethra 3 within the bladder 4 by the stent delivery system 8 illustrated in the various following Figures. A first embodiment of the stent delivery system is shown in more detail in FIG. 2. The stent delivery system 8 generally includes a catheter inner shaft 9, a catheter outer shaft 10, a peel away sheath 11, and a stent retainer 12 mounted on the catheter inner shaft just proximal of the stent 7 (hidden in this view under stent restrictor 13 and peel away sheath 11). The peel away sheath extends from the proximal end of the device to the distal end of the device, covering all the uneven surfaces of the stent, the anchor device, and the retainers. A stent restrictor 13 surrounds the stent and the peel away sheath in the area of the stent. An expandable mesh basket type anchor 14 is secured to the distal tip of the inner shaft 9 with basket mounting ring 15, and the proximal end of the basket is slidably mounted on the inner shaft 9 by sliding mounting ring 16. The mesh basket is made of plastic mesh with mesh fibers oriented diagonally around the circumference of the mesh tube, at an angle to the longitudinal and radial dimensions of the tube. When uncompressed, the mesh anchor forms a tube, as illustrated in FIG. 2, but when compressed longitudinally it takes on the toroidal shape shown in FIGS. 6 and 7, being preferentially disposed to take on this shape upon longitudinal compression.

Figure 2:
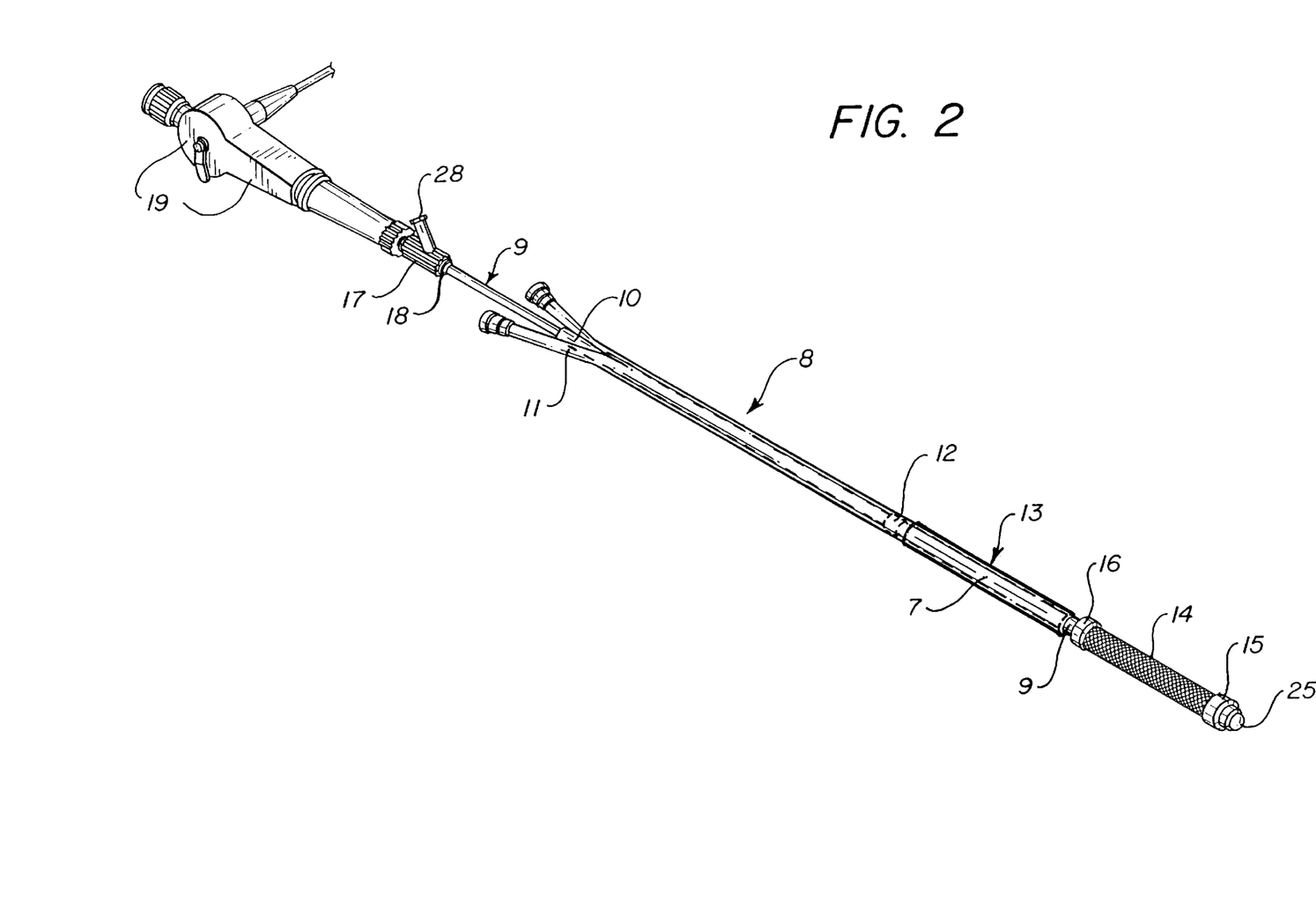
FIG. 2 shows a surface view of an embodiment of the stent delivery system.

The endoscope shown in FIG. 2 may be one of many conventional endoscopes. The endoscope is fitted into the delivery system through a scope adapter port 17, which is connected to the catheter inner shaft 9 at the catheter's proximal end 18. The endoscope 19, whether provided with the system or provided separately, also forms a part of the deployment system. (The term endoscope is used in this specification to denote any scope that may be used with the delivery system, although scopes of various designs are referred to by different names such as laparoscopes and cystoscopes.)

Figure 3:
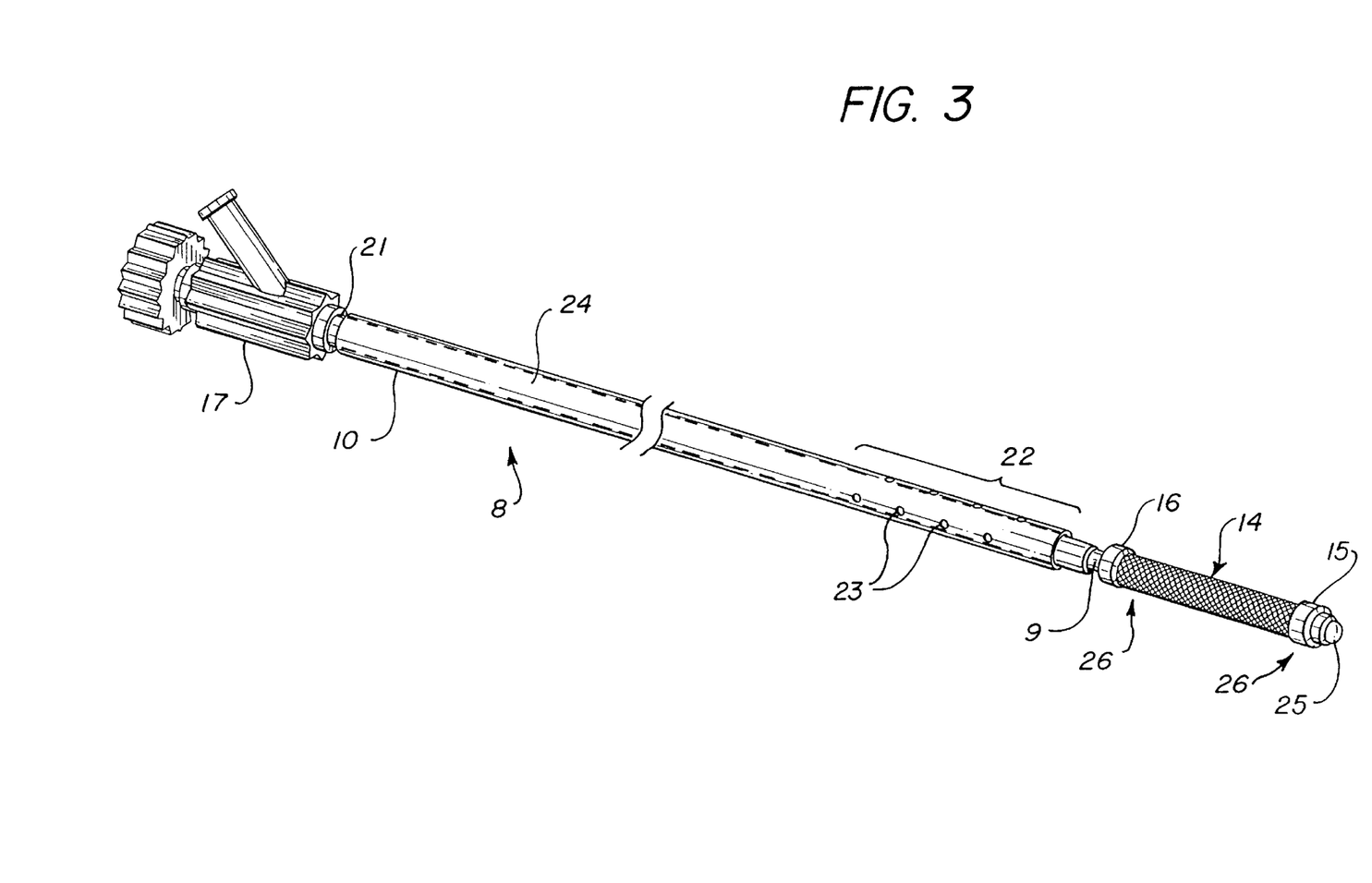
FIG. 3 shows a surface view of the inner and outer catheter shafts of the stent delivery system.
Figure 4:
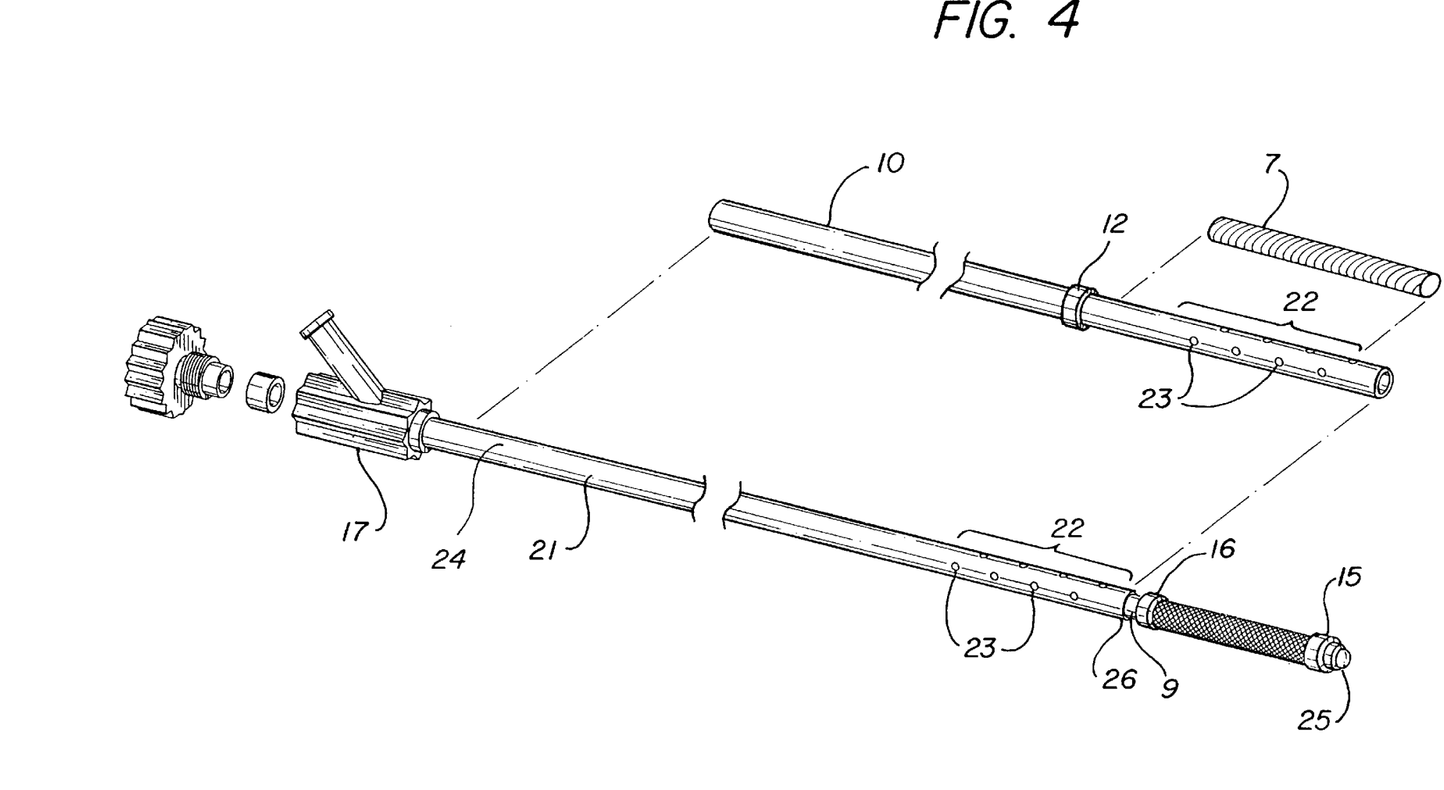
FIG. 4 shows an exploded view of the inner and outer catheter shafts of the stent delivery system.

The catheter inner and outer shafts are shown more clearly in FIGS. 3 and 4. Referring to FIG. 3, the stent delivery system 8 includes a urethral catheter with a single-lumen catheter inner shaft 9 made from a flexible, medical grade elastomer or thermoplastic. The catheter inner shaft 9 may be optically clear, at least in the stent loading zone 22 to allow for visualization of the prostatic urethra through the wall of the catheter shaft during insertion of the stent delivery system. The catheter inner shaft 9 is provided with vent holes 23 in a longitudinally and radially staggered pattern as shown in the exploded view of FIG. 4. The inner lumen 24 of the catheter inner shaft communicates with the scope adapter port 17 such that the endoscope slips inside of the scope adapter port and into the inner lumen to the stent loading zone 22. The inner lumen is sealed off by a suitable valve 25 (the valve may be a duckbill valve, bicuspid valve, tricuspid valve, or a ring seal) which prevents leakage during water injection. The catheter inner shaft 9 has an outer diameter of about 20 Fr, is preferably marked at 1 cm increments, and should be both long enough and flexible enough to permit insertion of the catheter's distal end 26 through the urethra and into the bladder. The inner shaft 9 is preferably about 35 cm in length with an internal diameter of at least 16 Fr in order to fit most types of endoscopes. The inner lumen should be configured such that the endoscope is capable of moving freely inside the catheter. At the same time, where the endoscope is to be used as a valve spool as described below, the inner lumen diameter should closely match the endoscope outer diameter to provide for a snug but slidable fit between the endoscope and the inner shaft. Suitable optically clear materials for the catheter inner shaft include polyurethane, polyethylene, PVC, and many other clear plastics.

Surrounding the catheter inner shaft 9 is a closely fitting outer shaft 10. The outer shaft 10 is radially and longitudinally slidable over the catheter inner shaft 9 and is provided with an array of vent holes 23*a* drilled in positions corresponding to the vent hole pattern of the catheter inner shaft 9. A slight bit of rotation or longitudinal movement will misalign the corresponding hole patterns of the catheter inner shaft and catheter outer shaft, and the alignment can be restored with a like amount of rotation and sliding. To facilitate alignment, the holes in the outer shaft may be elongated and enlarged relative to the vent holes on the catheter inner shaft. Like the inner shaft, the outer shaft 10 is made from a flexible, medical grade elastomer or thermoplastic and may be optically clear, at least in the stent loading zone 22. The stent 7 is wrapped around outer shaft 10 in the stent loading zone 22 between the stent retainer 12 and the slidable mounting ring 16.

Figure 5:
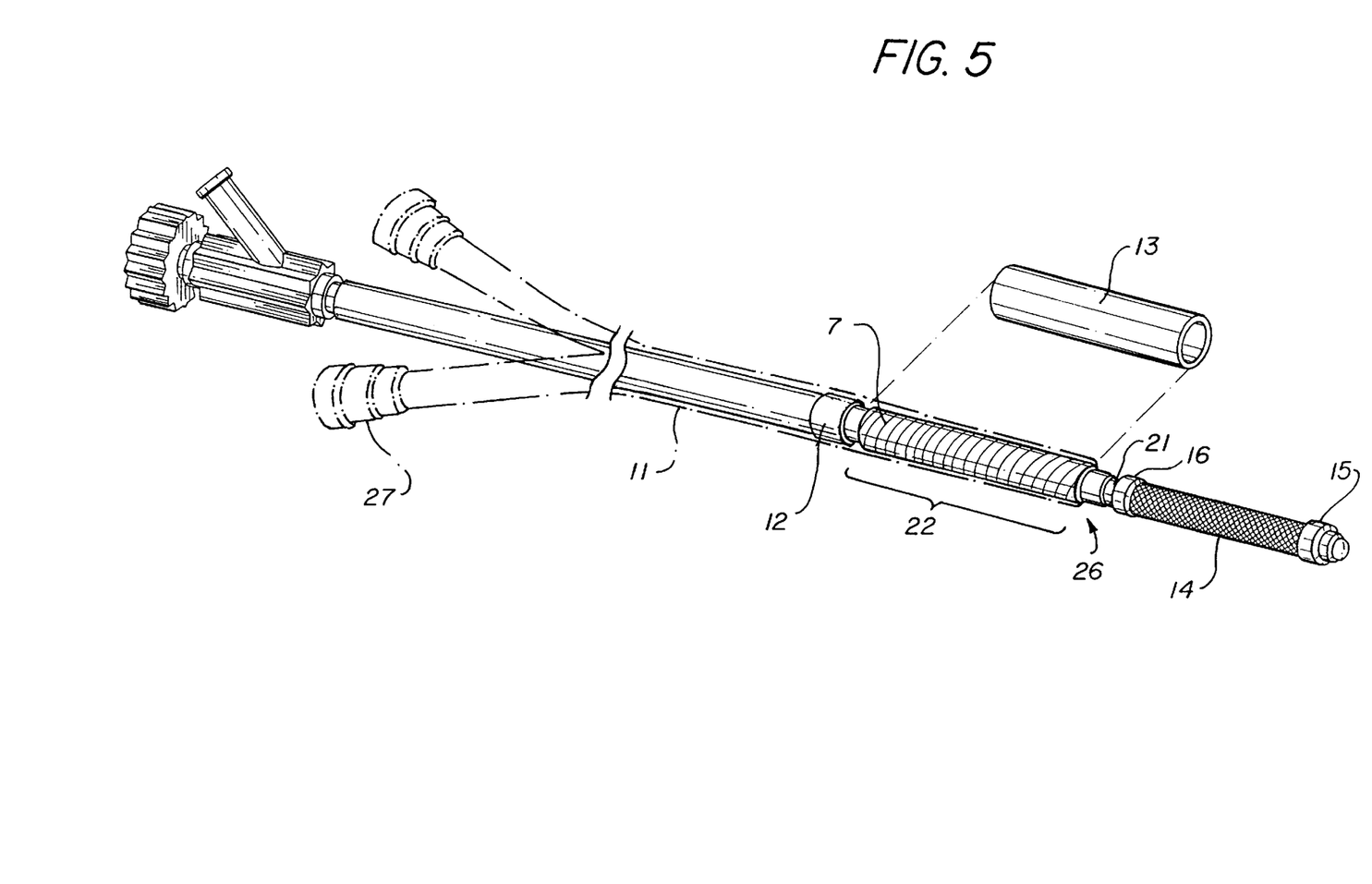
FIG. 5 shows an exploded view of the outer catheter shafts, stent, peel away sheath and stent restrictor of the stent delivery system.

Now referring to the exploded view of FIG. 5, the stent 7 is tightly wound around the catheter outer shaft at stent loading zone 22 near the catheter's distal end 26. The stent retainer 12 is fixed to the catheter outer shaft and retains the stent in place and prevents longitudinal movement during handling and insertion into the urethra. The diameter of the stent retainer 12 should be compatible with the diameters of the catheter and the peel away sheath, and its length may be variable, being just about 1 cm long, as shown, or extending all the way to the manifold at the proximal end of the catheter. The stent retainer 12 allows the position of the stent 7 to be adjustable along the catheter. The stent is best placed inside the prostatic urethra, downstream of the bladder neck sphincter, and the distance between the anchor and the stent chosen and controlled during manufacture to approximate the desired distance between the bottom of the bladder and the desired release point for the stent at a location downstream of the bladder neck sphincter. The adjustment may be made upon manufacture, with the retainer being fixed to the catheter, or the adjustment may be made by the treating physician just prior to the procedure, with the retainer being slidably mounted upon the catheter (in which case the friction fit should be fairly tight to avoid inadvertent movement).

The peel away sheath 11 is placed over the length of the catheter, including the stent 7, and possibly the mesh anchor 14. The stent restrictor 13 is placed over the peel away sheath to cover the loaded stent. The peel away sheath 11 is provided to cover the stent during placement and provide a smooth outer surface to facilitate placement of the stent 7. The peel away sheath 11 extends the length of catheter and is formed from a polyethylene terepthalate (PET) material, and many other materials may be used. The peel away sheath should be easily removable from the urethra by pulling on the peel away sheath's pull tabs 27 located at the proximal end of the peel away sheath. The stent restrictor 13 shown in FIG. 5 is designed to prevent incidental radial expansion of the stent during sterilization or shipping. Its inner diameter may be slightly larger than that of the peel away sheath. Its length should correspond to the length of the stent.

The loaded stent has a small diameter of about 1 cm that fits easily into the urethra. The stent 7 is made of a Nitinol alloy with a soft and pliable martensite transition temperature slightly below body temperature, in the range of 30–35° C. The transition temperature for the change to the austenitic state upon heating is slightly above body temperature, in the range of 38–60° C. That temperature range can be easily achieved by flushing hot saline through a catheter into the vicinity of the stent. The loaded stent is in the martensitic state, and is in the small diameter insertion configuration. The stent is trained (provided with a shape memory) to expand to a larger diameter deployed configuration of approximately 2–3 cm when heated to the austenite state.

Figure 6:
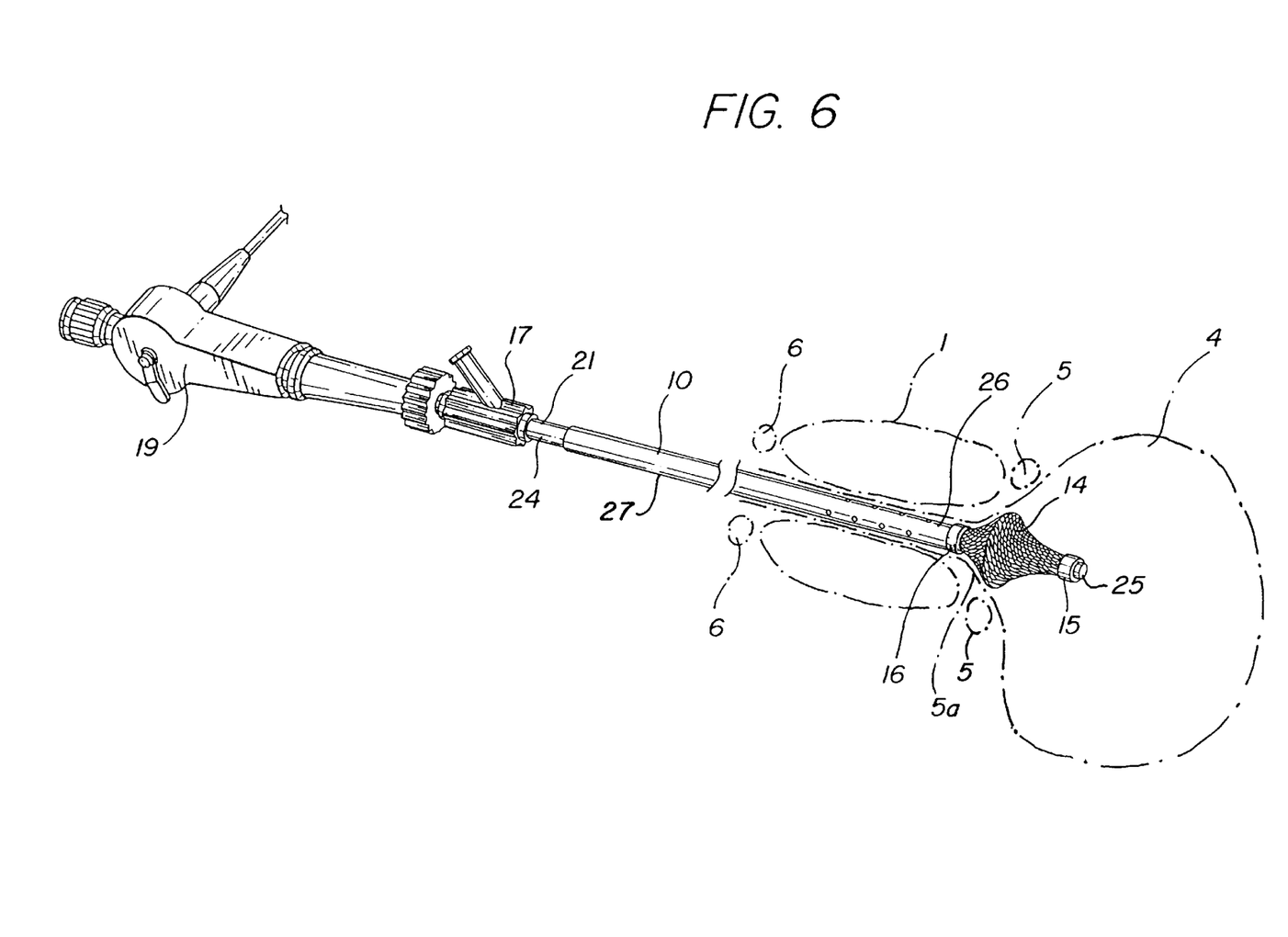
FIG. 6 illustrates the use of the stent delivery system with the mesh basket anchor in the expanded shape.
Figure 7:
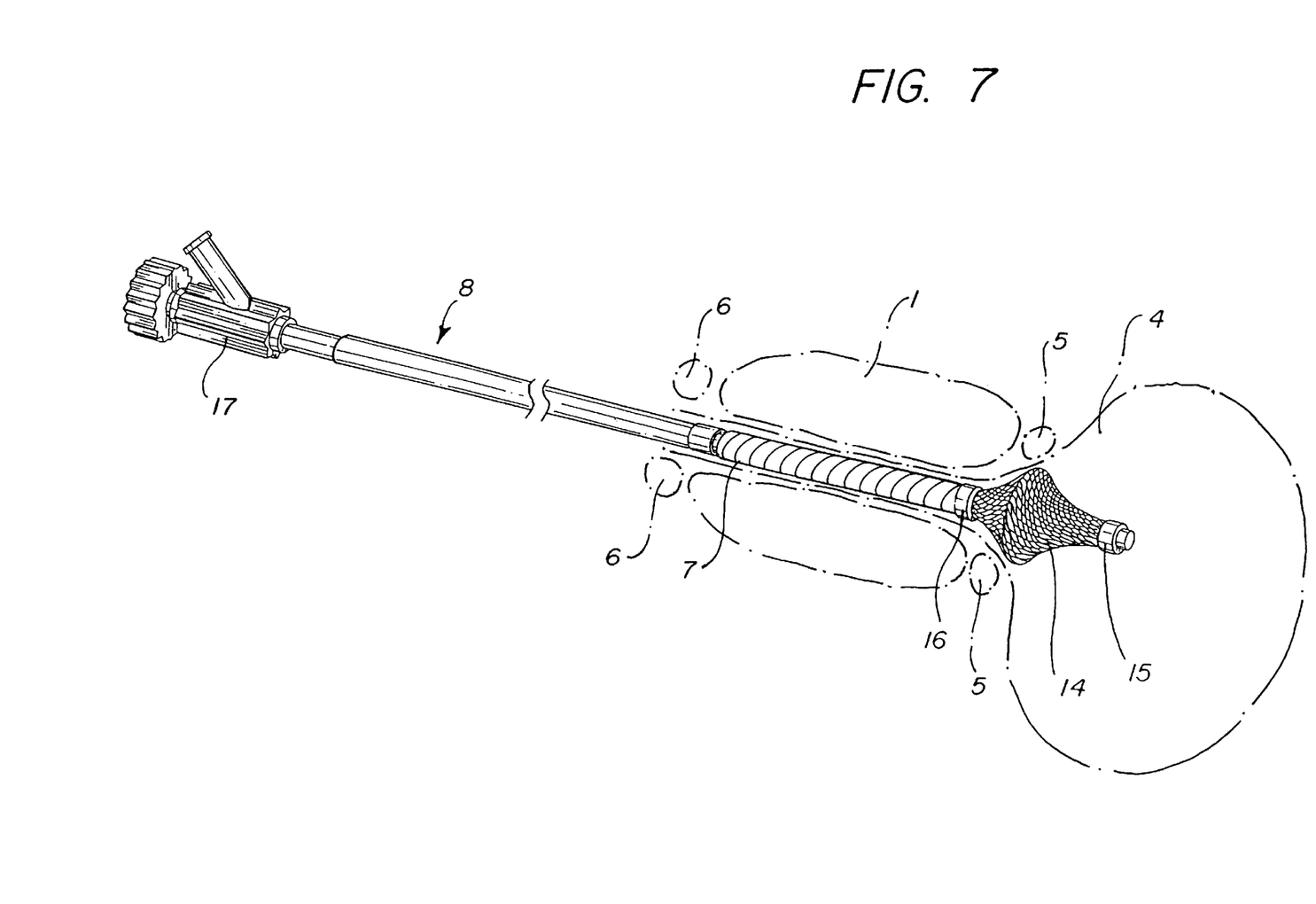
FIG. 7 illustrates the use of the stent delivery system with the mesh basket anchor in the expanded shape within the bladder.
Figure 8:
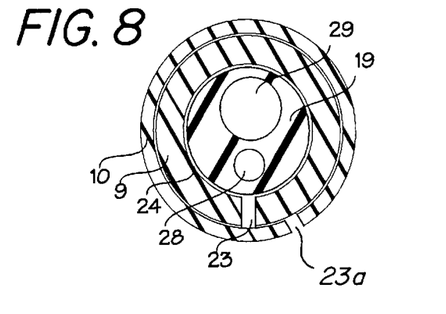
FIG. 8 is a radial cross section of the catheter shaft.

The mesh basket 14 is made of a plastic mesh and is tubular shaped during stent insertion. The mesh basket 14 is connected to the catheter shaft 9 at the catheter's distal end 26. The mesh basket 14 is toroidal shaped when expanded, as shown in FIG. 6. The mesh basket is expanded by pushing the catheter outer shaft 10 distally over the catheter inner shaft 9 such that the outer shell pushes against the sliding mounting ring 16 on the mesh basket until it is expanded. (In an alternative configuration, the mesh basket could be replaced with a malecot that is expanded in similar fashion). The endoscope 19 is inserted through the scope adapter port 17 and into the inner lumen 24 to provide a visual picture of the urethra. In this configuration, the endoscope 19 should have a working channel and an optics channel. FIG. 8 shows a partial radial cross section of the delivery system in the area of the stent loading zone, including the endoscope 19 with working channel 28 and optics channel 29, catheter inner shaft 9 with venting holes 23, and the catheter outer shaft 10 with venting holes 23a. A fluid supply path is created through the working channel 28, into the catheter inner shaft lumen 24 and into the venting holes 23 and 23a, coming in contact with the stent outside the catheter outer shaft 10.

In practice, the stent restrictor is removed prior to use. A guidewire may be inserted before the delivery system is inserted if the prostatic urethra is severely occluded, in which case the delivery system can be back loaded onto the guidewire and inserted over the wire into the prostatic urethra. The stent delivery system 8 is inserted through the patient's urethra 2 such that the mesh basket 14 enters the patient's bladder 4, as shown in FIGS. 1 and 6. The mesh basket is then expanded in the patient's bladder (by sliding the catheter outer sheath distally while holding the catheter inner sheath in place) and the delivery system is secured in place. The proximal face of the toroidal anchor mechanism formed by longitudinal compression of the mesh tube has a horn shape, sometimes referred to by doctors as a cornual shape. The cornual shape matches the typical shape of lumen of the bladder neck 5a which is a cornu (horn shaped anatomical structure) and provides a seating surface for the mesh basket to provide sure contact between the mesh basket and the bladder neck. The longitudinal distance between the distal end of the stent and the proximal face of the anchor mechanism approximates the expected length of the bladder neck, to ensure that, when the anchor mechanism is pulled to seat against the bladder neck, the distal end of the stent does not protrude into the bladder neck.

After the mesh basket is expanded inside the patient's bladder, it should be stable enough to anchor the stent delivery system in place such that no major movement of the stent delivery system will occur in the urethra. The proximal face of the now toroidal mesh basket is seated against the bladder neck sphincter 5, and the distance between the stent and the mesh basket is large enough to ensure that the stent is not within the lumen of the bladder neck sphincter, so that it cannot interfere with normal operation of the bladder neck sphincter. The length of the stent can also be limited so that it does not extend distally into the external sphincter 6 after deployment. When the delivery system is securely anchored, the peel away sheath is pulled proximally to expose the stent, and the system is in the configuration shown in FIG. 7. If a guidewire was used, it is withdrawn to permit insertion of an endoscope into the catheter. The distal valve 25 seals the distal tip of the catheter. The endoscope, if not already inserted, may now be inserted through the endoscope port and into the distal end of the catheter. The endoscope may be used to view the anatomical structures of the bladder, urethra, bladder neck sphincter and external sphincter, as well as the structures of the stent delivery system. It is expected that the desired position of the stent will be within the prostatic urethra, clear of the external sphincter and bladder neck sphincter.

Once the catheter and stent have been positioned with the aid of the endoscope, the stent may be released. The outer catheter shaft 10 is rotated until the vent ports 23a correspond to the vent ports 23 of the inner shaft 9. Warm saline is then injected into the working channel of the endoscope and thus to the inner lumen 24 of the catheter inner shaft 9.

Figure 9:
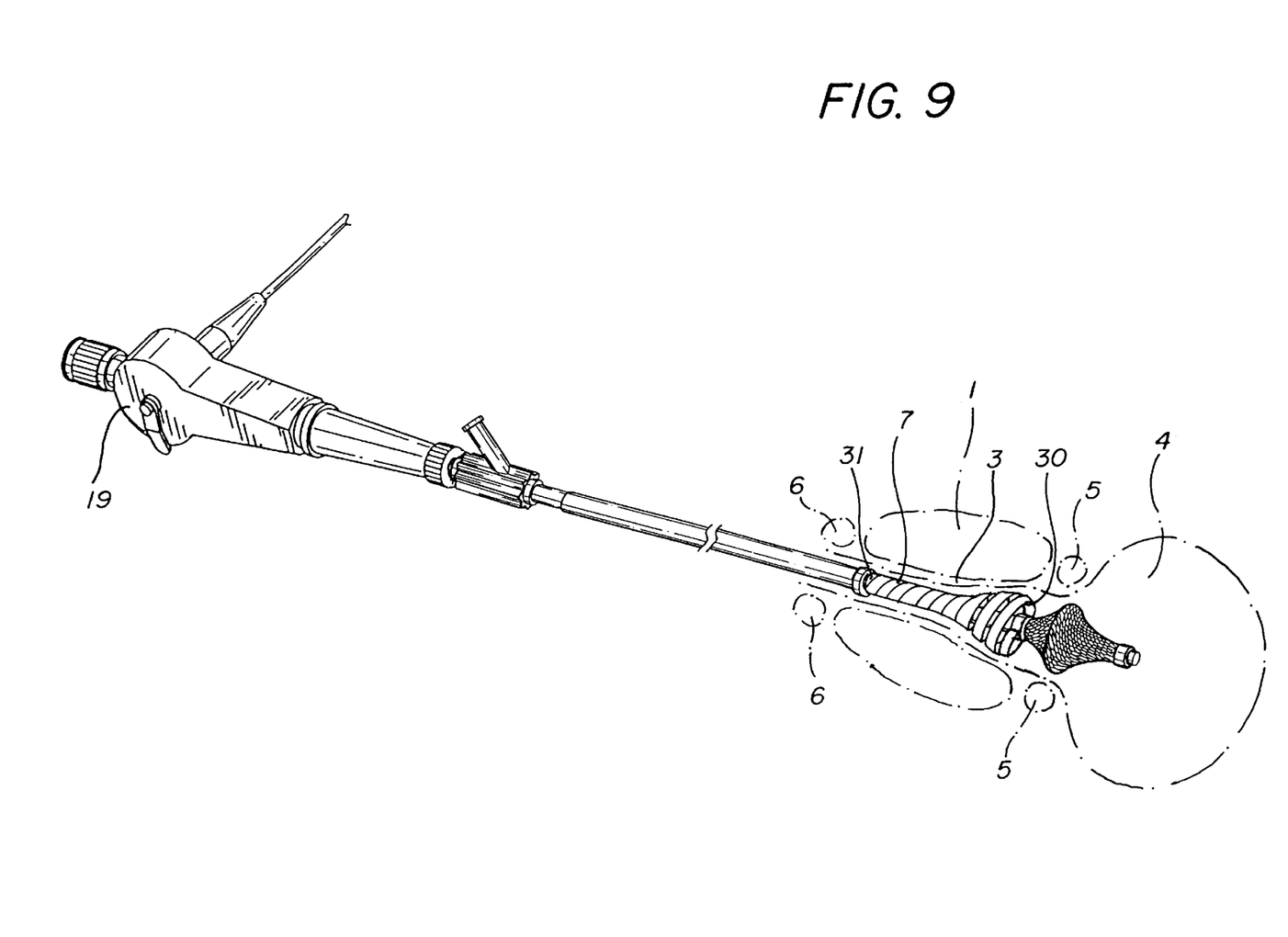
FIG. 9 illustrates the use of the stent delivery system with an expandable mesh anchor.

Because the endoscope outer diameter closely matches the diameter of lumen 24, the endoscope blocks the flow of warm fluid through the flow ports 23 unless it is withdrawn proximally to uncover the flow ports. Thus the endoscope serves as a valve spool, regulating the flow of fluid from the inner lumen into the flow ports. To expand the distal end of the stent before expanding other portions of the stent, the operator of the device will withdraw the endoscope slightly so as to uncover the most distal flow ports, causing warm fluid to flow over and warm the distal end of the stent. Warming of the stent will cause the stent to heat up above its austenite transition temperature. Upon this transition, the stent expands to the large diameter deployed configuration. Preferably, the distal coils of the stent recover their original large diameter shape first, as shown in FIG. 9. Proper positioning and seating of the stent within the prostatic urethra can be verified through the endoscope. As the endoscope 19 is pulled back out of the catheter to uncover more venting holes, those holes direct flow to more proximal portions of the stent, causing more proximal areas of the stent to heat up and revert to the memorized shape. The stent will expand radially, starting at the distal end 30 and progressing to the proximal end 31, and thereby anchor itself into the prostatic urethra 3 and hold the prostatic urethra open against the occlusive pressure of the prostate. Thus, control of the placement of the stent is readily achieved, and placement of the stent within the bladder neck sphincter is avoided. At the end of the procedure, the warm fluid flow is stopped, the endoscope extracted, the mesh basket or malecot is put back in its original tubular shape by pushing the catheter distally inside of the catheter outer shaft. The stent delivery system is withdrawn, leaving the stent in place.

Figure 10:
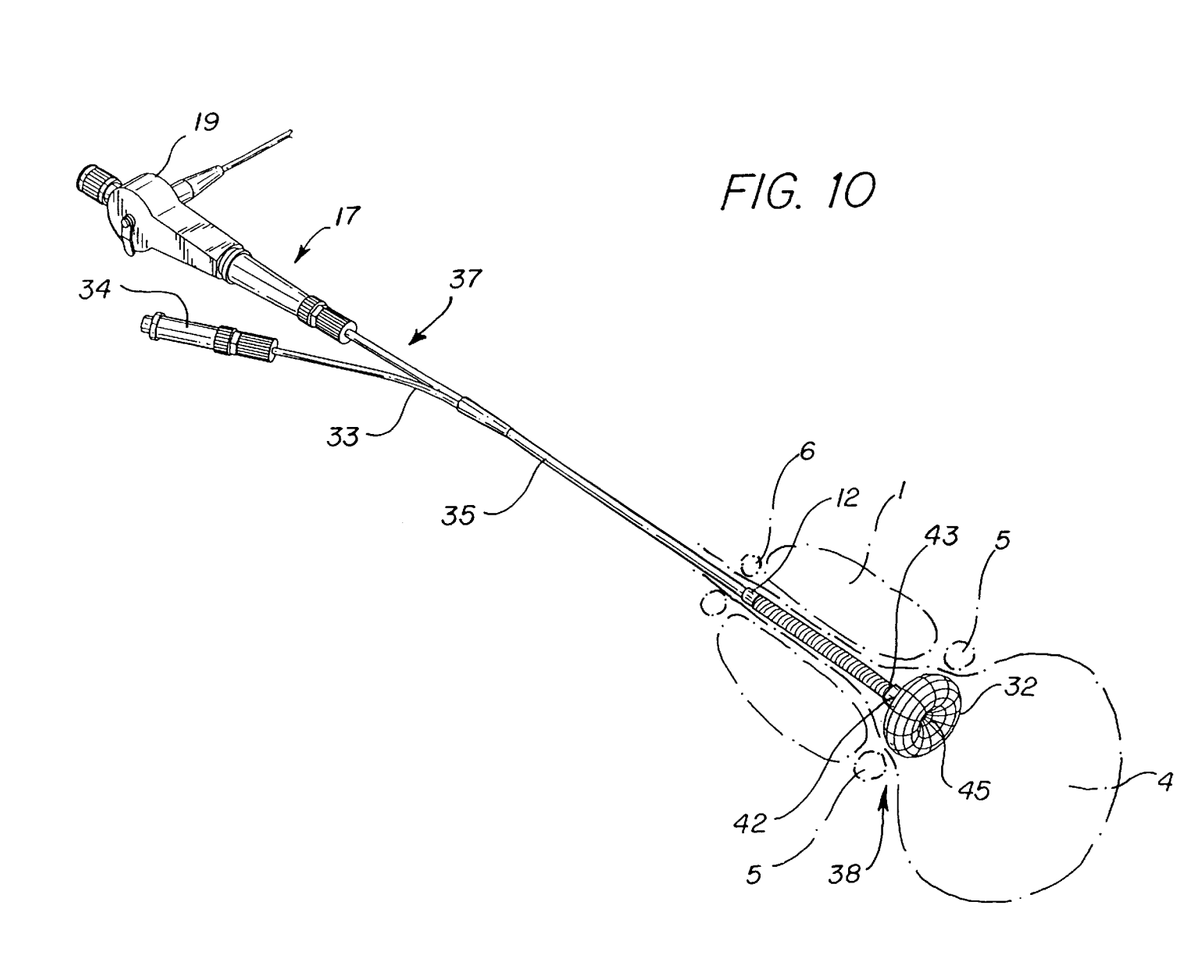
FIG. 10 illustrates an embodiment of the stent delivery system with a balloon anchor.
Figure 11:
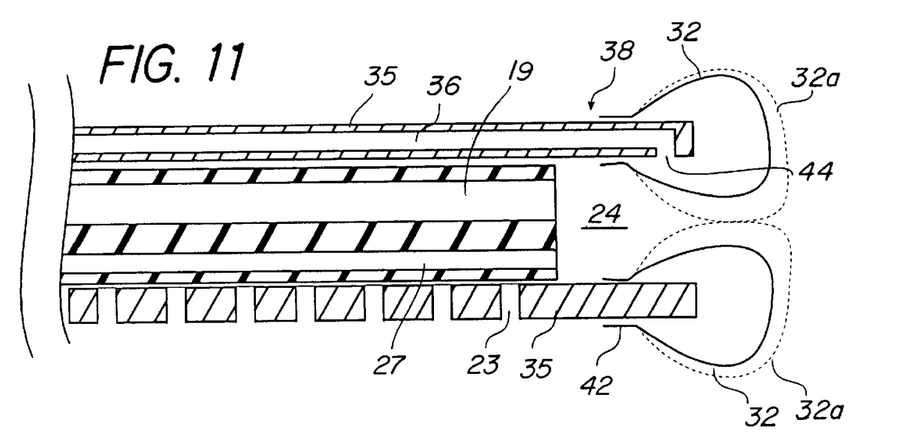
FIG. 11 is a cross section of the stent delivery system with a balloon anchor designed for use with an endoscope having a working channel.
Figure 12:
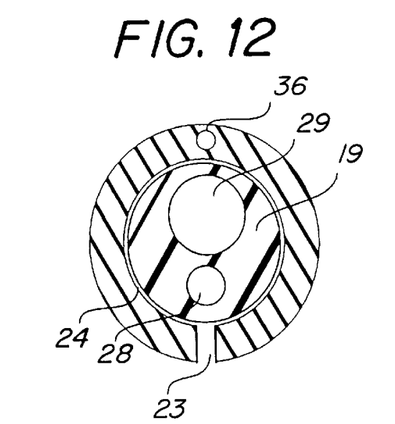
FIG. 12 is radial cross section of the stent delivery system of FIG. 11.

In an alternate configuration shown in FIG. 10, the mesh basket or malecot is replaced with a retention balloon 32. This configuration requires a dual-port manifold 33 providing a balloon inflation port 34 to inflate the balloon. This configuration also requires a multi-lumen catheter shaft 35, providing a balloon inflation lumen 36 (shown in the cross section of FIG. 11) in addition to the inner lumen 24 which accommodates the endoscope. The balloon inflation port 34 communicates with the balloon inflation lumen 36. The inner lumen 24 communicates with the working channel 27 of the endoscope which in turn communicates with the scope adapter port 17. The lumens extend substantially from the catheter's proximal end 37 to the catheter distal end 38. FIG. 11 shows a longitudinal cross section of this embodiment and FIG. 12 shows and radial cross section of the stent loading zone of the catheter. As in the preferred embodiment, the catheter shaft 35 is provided with diffuser holes 23 and is optically clear in the stent region. The endoscope serves as a valve spool for controlling flow of warm fluid out of the diffuser holes 23. This system is illustrated without the outer catheter shaft (item 10 of the earlier figures) to illustrate that the device is operational without the outer catheter shaft.

Figure 13:
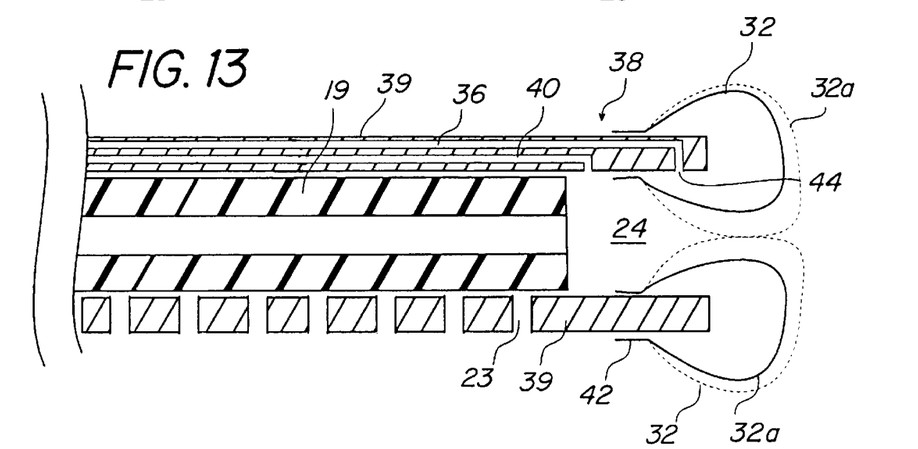
FIG. 13 is a cross section of the stent delivery system with a balloon anchor designed for use with an endoscope without a working channel.
Figure 14:
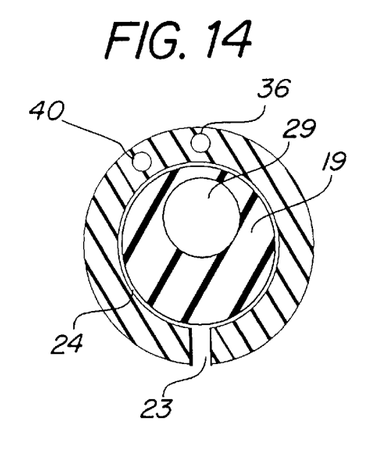
FIG. 14 is radial cross section of the stent delivery system of FIG. 13.

FIG. 13 shows a longitudinal cross section and FIG. 14 a radial cross section of the distal end of a third embodiment for the catheter for use again with the retention balloon. As shown, this multi-lumen catheter shaft 39 includes a balloon inflation lumen 36 and an inner lumen 24 for the endoscope as in the previous configuration, but this configuration also contains a separate warming fluid lumen 40 for use where the endoscope does not have a working channel. In this configuration, the water travels from a warming fluid inlet port, shown in FIG. 15, and into the warming fluid lumen 40 instead of the working channel of the endoscope.

Figure 15:
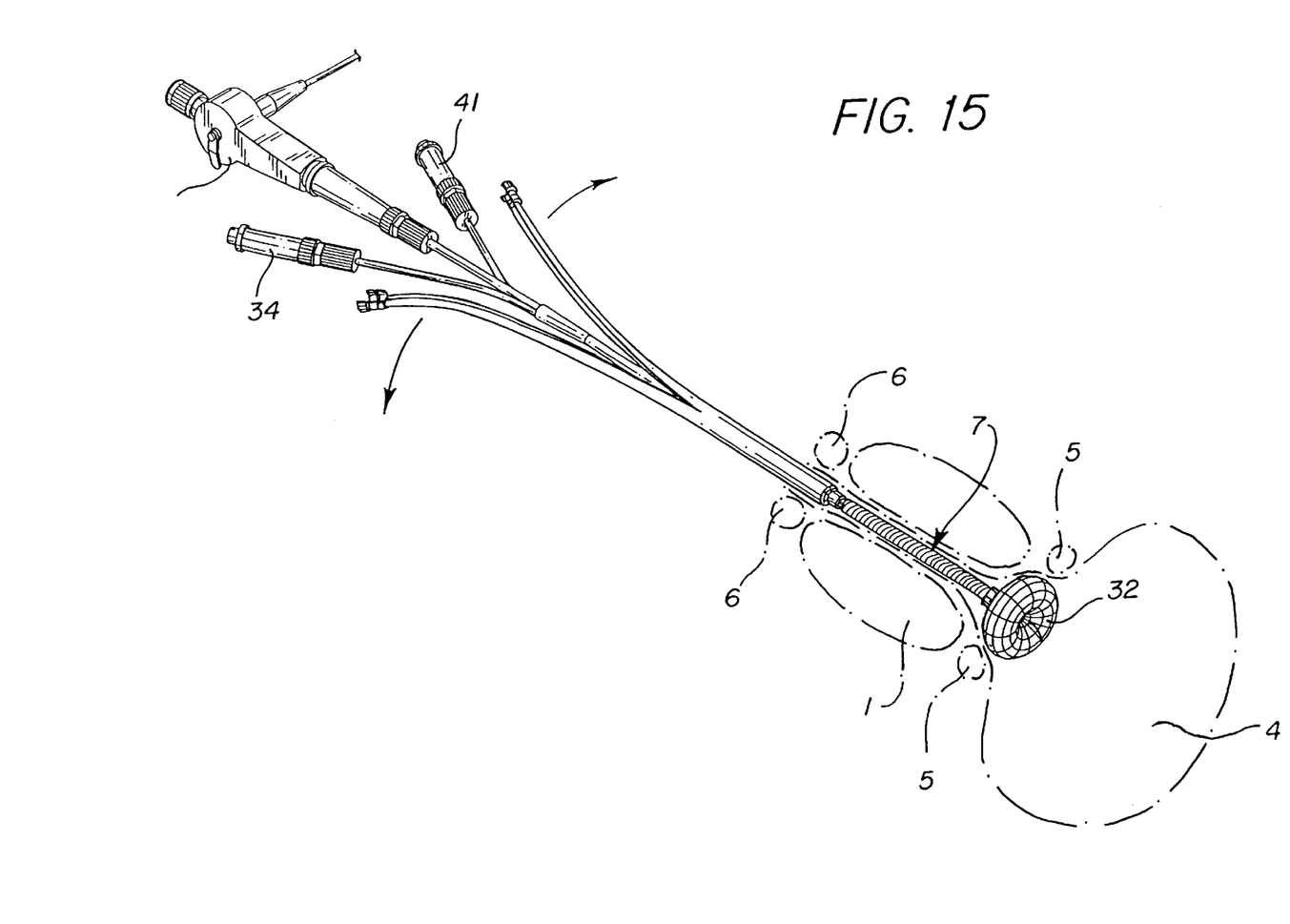
FIGS. 15 is a surface view of the stent delivery system of FIG. 10.

The expanded retention balloons 32 shown in FIGS. 10 and 15, are toroidal shaped and formed from a toroidal sleeve of an elastomer such as silicone or non-elastomer such as polyester. It is secured over the catheter shaft by bonding balloon waists 42 over the exterior surface of the shaft near the catheter's distal end 38. The balloon inflation lumen 36 communicates with the inflation port 34 and the interior of the balloon by opening 44, as shown in FIGS. 11 and 13. The retention balloon 32 is inflatable with any fluid using a small syringe. As can be seen in the cross sections of FIGS. 11 and 13, the inflation of the toroidal balloon closes off the distal end of the inner lumen 24, so that warming fluid flow will be directed to the venting holes 23. The inflated balloon configuration is shown in phantom lines 32a in FIGS. 11 and 13.

As shown in FIGS. 10 and 15, the stent delivery system is inserted through the patient's urethra as before, such that the retention balloon 32 enters the patient's bladder 4. The balloon 32 is then inflated with inflation fluid via the inflation port 34 and anchors the stent delivery system in place. The inflated retention balloon 32 should also be able to seal off the inner lumen 24 at the catheter's distal tip to prevent leakage during water injection, such that a seal or valve is not necessary in this configuration.

Figure 16:
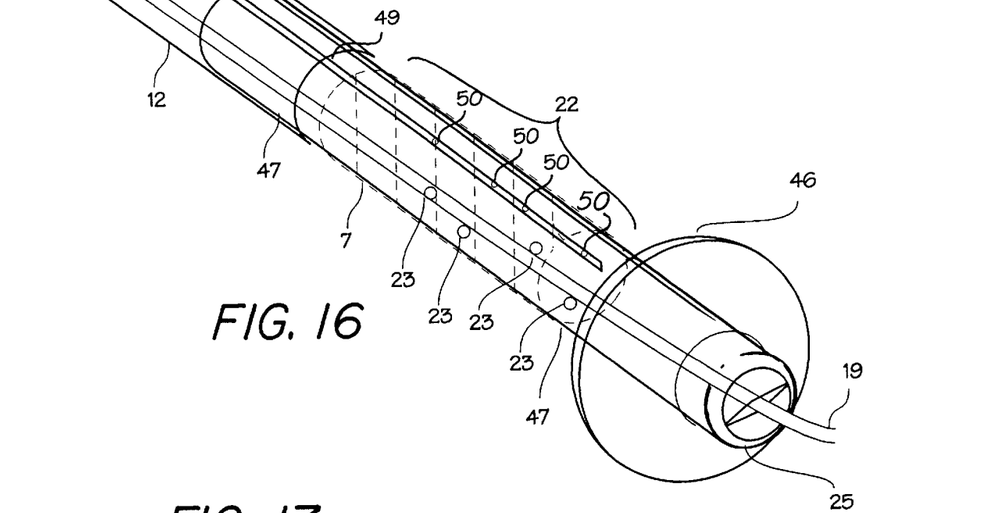
FIG. 16 shows a surface view of the stent delivery system employing a balloon anchor and a separate distal valve.

The stent delivery system illustrated in FIG. 16 is a simple embodiment of the stent delivery system. The anchoring means comprises the circumferential retention balloon 46 mounted at the distal tip of the catheter. The catheter inner shaft 47 is provided with venting holes 23 in a longitudinally and radially staggered pattern as shown in the prior figures. The inner lumen of the catheter inner shaft communicates with the scope adapter port 17 (not shown in this view) such that the endoscope slips inside of the scope adapter port and into the inner lumen to the stent loading zone 22. The inner lumen is sealed off by a suitable valve 25 (the valve may be a duckbill valve, bicuspid valve, tricuspid valve, or a ring seal) which prevents leakage during water injection. In this embodiment, the balloon, though toroidal, is not positioned at the very edge of the distal tip (as it is in FIG. 10), and so does not serve as a valve for the distal end of the inner lumen 24. Heating fluid injection port 48 communicates with the side mounted secondary fluid injection tube 49 which is provided with vent holes 50. As illustrated, the side mounted fluid injection tube is a separate tube, but it may readily be replaced with a side lumen in the wall of catheter shaft 47. The endoscope 19 with a working channel may be inserted into the inner lumen and through the valve 25.

Figure 17:
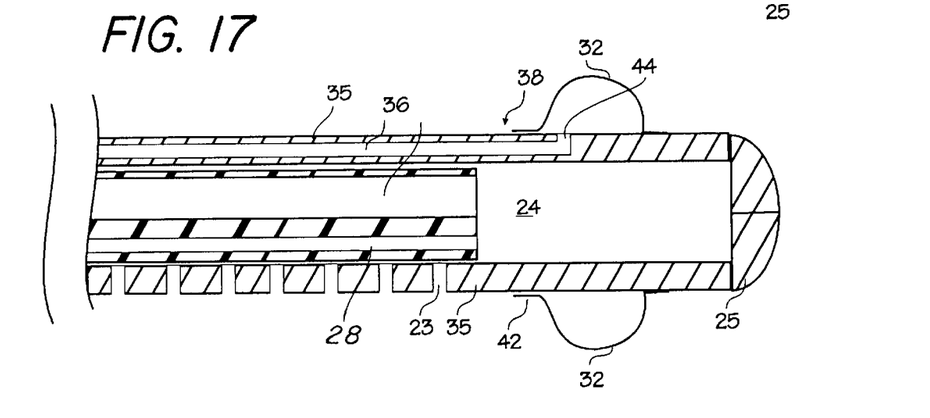
FIG. 17 is a longitudinal cross section of the stent delivery system of FIG. 16

FIG. 17 is a longitudinal cross section of the stent delivery system illustrated in FIG. 16. In this view, the placement of the retention balloon 32 is distal of the extreme distal tip of the catheter, and the distal sealing valve 25 is shown in the closed position. The catheter shaft 35 and balloon inflation lumen 36, the diffuser holes 23, and an inner lumen 24 are similar to the previous embodiments. The placement of the endoscope 19 with a working channel 28 are similar to the previous embodiments.

In use, the device of FIG. 16 is inserted into the urethra until the retention balloon is inside the bladder. Placement of the balloon is verified by visual inspection of the bladder through the endoscope which extends through the valve and out the distal end of the catheter as needed for proper viewing. The balloon may then be inflated to anchor the device in place, with the proper position relative to the bladder and the bladder neck sphincter verified by viewing through the endoscope within the bladder and within the prostatic urethra through the transparent catheter. Warm fluid may then be injected into the inner lumen through the working channel of the endoscope, and the warming fluid will flow through the vent holes to warm the stent and cause the stent to expand. The endoscope may remain in the inner lumen of the catheter and serve as a throttle to the proximal vent holes, and the warming fluid will preferentially flow through the distal vent holes. This provides for warming of the stent from the distal end of the device first, and then progressively warming the stent from the distal end to the proximal end. The stent may also be expanded with warming fluid flowing to the stent through the secondary injection tube. Where all the vent holes in the secondary injection tube are the same size, the warming fluid flow will be strongest in proximal region of the stent, so that the stent will expand first at the proximal end and then gradually expand from the proximal end to the distal end. The secondary fluid injection tube can also be used to provide an additional flow of warming fluid to ensure that the stent is fully heated and expanded.

Figure 18:
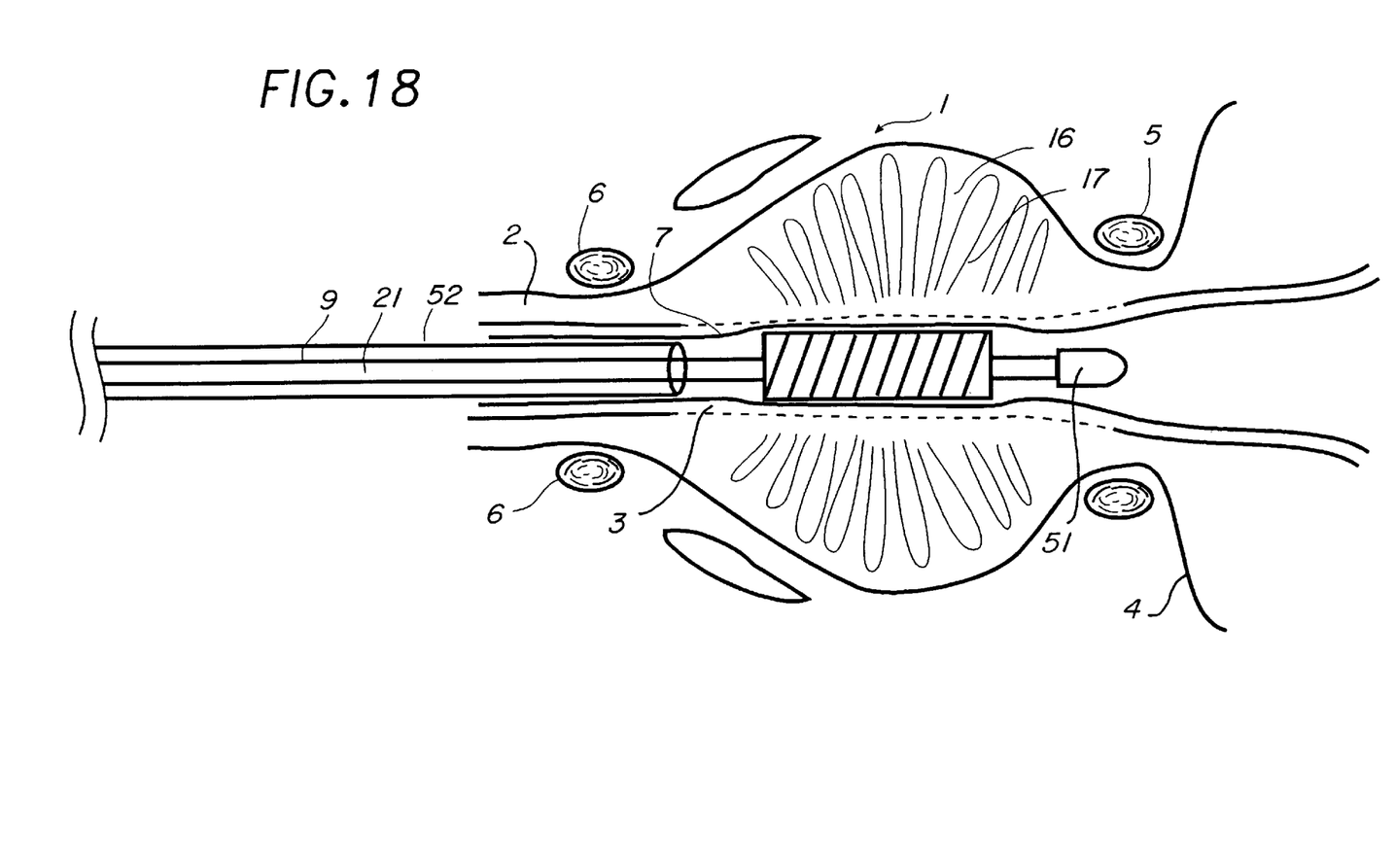
FIG. 18 illustrates the method of removing the stent after use.

FIG. 18 shows the stent 7 in place in the urethra 3. The bladder neck sphincter 5 and external sphincter 6 close the urethra off from the bladder 4, which is necessary for continence. The prostatic urethra 3 is maintained patent by the opened stent, and the patient provided relief from the discomfort and danger of the swollen prostate, while the bladder neck 5a remains clear of obstruction so that normal physiological operation of the bladder neck sphincter to close off the bladder neck is allowed, and the patient remains continent.

In regards to each embodiment illustrated above, the mechanisms which enable anchoring the stent before deployment may be beneficially employed with any type of stent, including self expanding and balloon expanded stents. The mechanisms which permit controlled flow of warming fluid to the shape memory stent may also be employed in the absence of the anchoring mechanisms.

After the stent has served its purpose, it is removed in order to avoid infection. Removal of the stent is accomplished by inserting the stent delivery system 8 into the urethra 2 until the anchoring mechanism 51 (shown schematically in FIG. 18) enters the bladder, whereupon it is expanded to anchor the catheter in place. Flushing the stent with cold saline solution delivered through a scope or through the retrieval sheath 52 cools the stent to cause reversion of the stent into the soft, pliable martensite state. The endoscope is inserted through the scope adapter port to find and remove the stent. A retrieval sheath is gently pushed over the stent, and graspers can be inserted through the endoscope working channel to grasp the stent and hold it in place or actively pull the stent into the retrieval sheath. The cold stent is soft and pliable and offers little resistance to the sheath or the graspers. The expanded anchor mechanism prevents accidental insertion of the stent into the bladder because it occludes the bladder neck. When the stent has been removed, the anchor mechanism can be returned to its small diameter insertion configuration and the catheter is removed from the urethra.

In regards to each embodiment illustrated above, the mechanisms which enable anchoring the stent before deployment may be beneficially employed with any type of stent, including self expanding and balloon expanded stents. The mechanisms which permit controlled flow of warming fluid to the shape memory stent may also be employed in the absence of the anchoring mechanisms. The transition temperature of the shape memory stent may be any temperature suitable for use, including temperatures below body temperature or significantly above body temperature.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A stent delivery system for use in delivering a stent into the prostatic urethra, through the urethra, while avoiding placement of the stent across the bladder neck sphincter or protruding into the bladder, said stent delivery system to be used in conjunction with an endoscope, said stent delivery system comprising:

a catheter having a proximal and distal end and a distal tip, an anchor at the catheter's distal end, said catheter being optically clear near the distal end, said catheter having longitudinally spaced diffuser holes near the distal end, said catheter having a lumen extending from the proximal end of the catheter to the distal tip of the catheter;

said catheter having a lumen extending from the proximal end of the catheter to the distal end of the catheter, said catheter having a valve operable to close the lumen at the distal tip, an outer catheter shaft slidably disposed upon said catheter, said outer catheter shaft being optically clear near the distal end, said outer catheter shaft having diffuser holes near the distal end thereof which correspond to the diffuser holes of the catheter;

said lumen having a diameter sufficient to accommodate an endoscope in a slidable manner within the lumen, said endoscope serving to block the diffuser holes in the catheter distal end when placed in a longitudinal position within the lumen corresponding to the diffuser holes, and also being operable to open the diffuser holes by longitudinal movement of the endoscope within the catheter.

2. A stent delivery system for use in delivering a stent into the prostatic urethra, through the urethra, while avoiding placement of the stent across the bladder neck sphincter or protruding into the bladder, said stent delivery system to be used in conjunction with an endoscope, said stent delivery system comprising:

a catheter having a proximal and distal end and a distal tip, an anchor at the catheter's distal end, said catheter being optically clear near the distal end, said catheter having longitudinally spaced diffuser holes near the distal end, said catheter having a lumen extending from the proximal end of the catheter to the distal tip of the catheter;

a catheter having a proximal and distal end, an anchor at the catheter's distal end, said catheter being optically clear near the distal end, said catheter having longitudinally spaced diffuser holes near the distal end;

said catheter having a lumen extending from the proximal end of the catheter to the distal end of the catheter, said catheter having a valve operable to close the lumen at the distal tip, an outer catheter shaft slidably disposed upon said catheter, said outer catheter shaft being optically clear near the distal end, said outer catheter shaft having diffuser holes near the distal end thereof which correspond to the diffuser holes of the catheter;

said lumen having a diameter sufficient to accommodate an endoscope in a slidable manner within the lumen, said endoscope serving to at least partially block the diffuser holes in the catheter distal end when placed in a longitudinal position within the lumen corresponding to the diffuser holes, and also being operable to open the diffuser holes by longitudinal movement of the endoscope within the catheter.

3. The stent delivery system of claim 1 or 2 wherein the anchor comprises an expandable mesh basket.

4. The stent delivery system of claim 1 or 2 wherein the anchor comprises an inflatable toroidal balloon.

5. The stent delivery system of claim 1 wherein the anchor comprises an inflatable toroidal balloon, and wherein the inflatable toroidal balloon also serves as the valve operable to close the lumen at the distal tip.

6. The stent delivery system of claim 2 wherein the anchor comprises an inflatable toroidal balloon, and wherein the inflatable toroidal balloon also serves as the valve operable to close the lumen at the distal tip.

7. The stent delivery system of claim 1 further comprising:

a stent retaining structure mounted on the catheter and having a diameter approximately equal to the diameter of a stent in its unexpanded configuration to be placed on the catheter, said retaining structure limiting any longitudinal movement of the stent upon the catheter.

8. The stent delivery system of claim 2 further comprising:

a stent retaining structure mounted on the catheter and having a diameter approximately equal to the diameter of a stent in its unexpanded configuration to be placed on the catheter, said retaining structure limiting any longitudinal movement of the stent upon the catheter.

* * * * *